United States Patent [19]

Filius

[11] Patent Number: 5,008,464

[45] Date of Patent: Apr. 16, 1991

[54] ANISOLE BROMINATION

[75] Inventor: Larry Filius, Muskegon, Mich.

[73] Assignee: East Short Chemical Company, Muskegon, Mich.

[21] Appl. No.: 529,682

[22] Filed: May 29, 1990

Related U.S. Application Data

[63] Continuation of Ser. No. 413,886, Sep. 27, 1989, abandoned.

[51] Int. Cl.$^5$ .............................................. C07C 41/00
[52] U.S. Cl. .................................................... 568/656
[58] Field of Search ........................................ 568/656

[56] References Cited

U.S. PATENT DOCUMENTS

| | | | |
|---|---|---|---|
| 2,607,802 | 8/1952 | Britton et al. | 260/544 |
| 3,256,350 | 6/1966 | McCall et al. | 260/650 |
| 3,426,035 | 2/1969 | Bremmer | 260/297 |
| 3,689,559 | 9/1972 | Taylor et al. | 260/562 R |
| 4,447,660 | 5/1984 | Jouannetaud et al. | 568/774 |
| 4,730,046 | 3/1988 | Leone-Bay et al. | 544/334 |

FOREIGN PATENT DOCUMENTS 2919234 11/1980 Fed. Rep. of Germany .

*Primary Examiner*—Bruce Gray
*Attorney, Agent, or Firm*—Benjamin Mieliulis

[57] ABSTRACT

An improved method for the production of 4-bromo-3-alkylanisole, particularly 4-bromo-3-methylanisole is described. The method involves establishing 3-alkylanisole as a vapor in a reaction zone of a reactor and establishing bromine as a vapor. Thereafter the bromine vapor is introduced to the reaction zone of the reactor and commingled with the established 3-alkylanisole vapor. Dibrominated impurity is substantially reduced.

12 Claims, 1 Drawing Sheet

ANISOLE BROMINATION

This application is a continuation of application Ser. No. 07/413,886, filed Sept. 2, 1989, now abandoned.

FIELD OF INVENTION

BACKGROUND OF INVENTION

This invention relates to bromination of aromatic compounds and more particularly relates to bromination of anisole compounds particularly alkylated anisoles. These brominated compounds are commercially useful in the manufacture of a variety of products, particularly in the synthesis of certain organic compounds such as various dyes.

DESCRIPTION OF RELATED ART

Present methods for bromination of 3-alkyl anisole, particularly 3-methyl-anisole involves liquid reaction of bromine and 3 methyl-anisole. Reaction is typically conducted at elevated temperature with one or both reactants dissolved in a solvent such as heptane, carbon tetrachloride, acetic acid or hydrogen bromide water solution of approximately 48% HBr.

Offenlegungsschrift 29 19 234 application Nov. 20, 1980 discloses a process for manufacture of p-bromoanisole by reacting anisole with a solution of bromine in an aqueous hydrogen bromide solution. The '234 process is said to reduce 2,4-dibromoanisole proportions. Earlier processes of producing p-bromoanisole are also discussed in the '234 application including solvent free reaction relying on an iron catalyst, and including reaction of anisole in glacial acetic acid as solvent. These prior art processes are characterized as contaminated with considerable amounts of 2,4-dibromoanisole.

The '234 application while improving over the earlier methods still has the drawback of dibromoanisole impurities in amounts more than are desirable (2.5% by weight).

Prior art methods have dibromoanisole contamination levels of 2.5 to 10%.

It would be an advance in the art if a method were found to appreciably reduce unwanted dibromo contamination in the manufacture of 4-bromo-3-alkylanisole from 3-alkylanisole.

It is an object of the present invention to disclose a lower cost, higher yield method for making 4-bromo-3-alkylanisoles.

The disclosed method of the invention has the advantage of eliminating solvent diluent, increases productivity, and eliminates or minimizes needs for subsequent product purification.

SUMMARY OF THE INVENTION

Figure 1:
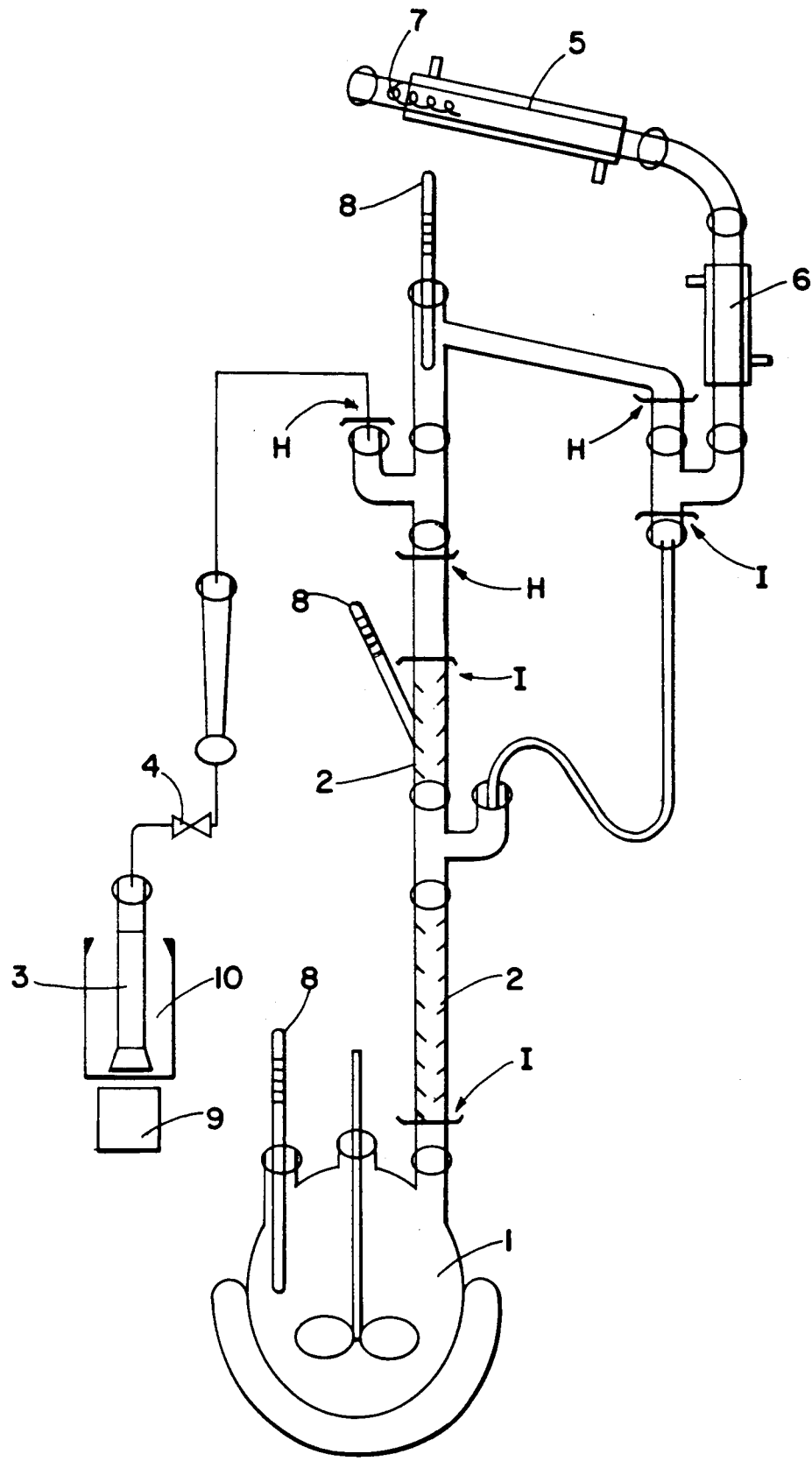
FIG. 1 is a vapor phase bromination apparatus useful for practicing the disclosed method of the invention.

The present invention discloses a novel method for the making of 4-bromo-3-alkylanisole, particularly 4-bromo-3-methylanisole. the alkyl group can be selected to be lower alkyl. Lower alkyl is defined as 8 carbons or less, preferably 5 carbons or less. The method comprises establishing a molar excess of 3-alkylanisole as a vapor in a reaction zone of a reactor. Bromine (b.p. 331° K.) is established as a vapor in the reactor and introduced to the reaction zone commingling with the established 3-alkylanisole vapor. 3-alkylanisole vapor enters the reaction zone, being at a slightly higher temperature, insures complete vaporization and the resultant production of 4-bromo-3-alkylanisole with almost no dibrominated impurity.

DETAILED DESCRIPTION

A method for making high purity 4-bromo-3-alkyl anisole, particularly, 4-bromo-3-methyl anisole is disclosed. The method involves introducing a 3-alkyl anisole such as 3-methyl anisole or other 1-8 carbon alkyl substituted anisole, into a reactor. The 3-alkyl anisole is then vaporized and directed to the reaction zone of the reactor. Vaporization can be accomplished by conventional means such as application of heat, and/or optionally reduction of reactor pressure, preferably both steps. Bromine vapor is generated from a bromine source such as by heating liquid $Br_2$ above its boiling point 331° Kelvin to form a gas. The bromine vapor is directed to and introduced to the reaction zone of the reactor wherein the vaporized 3-alkyl anisole is maintained in a gaseous phase. Such maintenance of 3-alkyl anisole in the gaseous phase is readily accomplishable by arranging a reflux of the partially reacted reaction zone effluent to the rectifying column, contined heat input to the reboiler, and maintenance of the reaction zone at about 10° to 30° C. higher temperature than the entering vapor. The resulting mixed vapors are maintained in the vapor phase, such as via reflux, for a time sufficient to react and convert the 3-alkyl anisole to 4-bromo-3-alkyl anisole.

Looking now at FIG. 1, a convenient reactor apparatus is depicted for effecting vapor phase anisole bromination according to the invention.

Round bottom flask 1 is provided with a thermometer 8 and stirrer and provided with distillation or reflux column 2. A bromine source 3 stirred by magnetic mixer 9 is maintained in a water bath 10 and via control valve 4 gas is inlet ultimately to the top of reflux column 2.

A vacuum is applied via condenser 5 which uses a cooling fluid of glycol at $-15°$ C. The condenser can be fitted with a glass wool demister. An optimal water condenser 6 can also be included. The 3-alkyl anisole is introduced to flask 1 and heated from about 90° to 150° C. The bromine source 3 is heated via a water bath. Column 2 is preferably maintained at about 90°-100° C. when the 3-alkyl anisole is selected to be 3-methyl anisole. The above temperatures are based on about 50 mm Hg pressure for the system. Higher applied vacuum of course would alter these recited temperature ranges. Points between the areas marked H have a heat tape applied. Points between areas marked I are insulated.

EXAMPLE

Using an apparatus such as depicted in FIG. 1, a round bottom flask 1 reboiler is charged with 329 g of neat 3-methyl-anisole. This charge can be varied within the capacity limits of the reboiler.

A bromine vaporizor is initially charged with 100 mls of $Br_2$ (its capacity) and later with the remaining 28.5 mls of Bromine.

The system is reduced to a pressure of 50 mm Hg, however 10 mm to about 200 mm is an acceptable range.

The reboiler is heated to effect reflux at about 5.5 mls/minute. The acceptable reflux rate range is about 1 ml to about 8 mls/minute.

The vapor reactor heat tape is turned on and the voltage adjusted just high enough to prevent condensation of 3-methylanisole in the vapor reactor.

The $Br_2$ feed valve is opened and adjusted to give 0.2 mls of vapor per minute. The acceptable range is between 0 and 0.5 mls/minute at the recommended system pressure of 50 mm Hg.

As the bromination progresses the temp of upper part of column remains constant (at about 90° C.) while the reboiler temp slowly rises from about 97° C.

When the reaction is just about done, the column temp will begin to rise. At this time the $Br_2$ addition rate is decreased to maintain a column temp of less than 100° C. (10° max. temperature rise for the column)

When the column temp exceeds a 10° C. differential and the $Br_2$ feed rate is at the lowest practical rate, the reaction is terminated.

The reboiler temp at this time is about 150° C. The total reaction time with this equipment and charge is 11 hours.

The crude product weight is 522 g.

The residual 3-methyl-anisole (about 1% to 5%) is distilled off with high reflux and recycled to the next bromination reaction.

A typical precut is 4.6% of crude weight or 24 g which contains about 22 g of 3-methyl-anisole to be recycled.

The remaining product (498 g) assays:
98% 4-bromo-3methyl-anisole
0.1% dibromo anisole
1.0% 3-methyl-anisole dimer and trimers
0.9% other impurities including bromo cresol (from cresol impurity in 3-methyl-anisole)

The final assayed yield is 488 g from 307 g of 3-methylanisole reacted or 96.6% reaction yield.

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes can be made by those skilled in the art without departing from the spirit and scope of the invention.

What is claimed is:

1. A method for making 4-bromo-3-alkylanisole comprising introducing 3-alkylanisole into a reactor having a reaction zone, establishing 3-alkylanisole as a substantially solvent-free vapor in the reaction zone of the reactor, introducing bromine vapor to the reaction zone of the reactor from a separate source of bromine and into the presence of the vaporized 3-alkylanisole to form mixed vapors, maintaining the mixed vapors in a vaporized phase for a time and a temperature sufficient to convert 3-alkylanisole to 4-bromo-3-alkylanisole.

2. The method according to claim 1 wherein the reaction zone of the reactor is maintained at a pressure of from 10 mm to 200 mm mercury.

3. The method according to claim 2 wherein the reaction zone of the reactor is maintained at about 50 mm Hg.

4. The method according to claim 1 wherein maintaining the mixed vapors in a vaporized phase is accomplished by refluxing the 3-alkylanisole in the reactor.

5. The method according to claim 1 wherein the temperature of the reaction zone is maintained at less than 100° C.

6. The method according to claim 5 wherein the reaction zone of the reactor is maintained at about 50 mm Hg pressure.

7. A method for making 4-bromo-methylanisole comprising introducing 3-methylanisole into a reactor having a reaction zone, establishing 3-methylanisole as a substantially solvent-free vapor in the reaction zone of the reactor, introducing bromine vapor to the reaction zone of the reactor from a separate source of bromine and into the presence of the vaporized 3-methylanisole to form mixed vapors, maintaining the mixed vapors in a vaporized phase for a time and a temperature sufficient to convert 3-methylanisole to 4-bromo-3-methylanisole.

8. The method according to claim 7 wherein the reaction zone of the reactor is maintained at a pressure of from 10 mm to 200 mm mercury.

9. The method according to claim 8 wherein the reaction zone of the reactor is maintained at about 50 mm Hg.

10. The method according to claim 7 wherein maintaining the mixed vapors in a vaporized phase is accomplished by refluxing the 3-methylanisole in the reactor.

11. The method according to claim 7 wherein the temperature of the reaction zone is maintained at less than 100° C.

12. The method according to claim 7 wherein the reaction zone of the reactor is maintained at about 50 mm Hg pressure.

* * * * *